United States Patent [19]

Karol

[11] Patent Number: 5,137,647
[45] Date of Patent: Aug. 11, 1992

[54] ORGANIC MOLYBDENUM COMPLEXES

[75] Inventor: Thomas J. Karol, Norwalk, Conn.

[73] Assignee: R. T. Vanderbilt Company, Inc., Norwalk, Conn.

[21] Appl. No.: 803,890

[22] Filed: Dec. 9, 1991

[51] Int. Cl.⁵ .................... C10M 139/06; C07F 11/00
[52] U.S. Cl. .................. 252/33.6; 252/42.7; 556/57
[58] Field of Search ................. 252/42.7, 33.6; 556/57

[56] References Cited

U.S. PATENT DOCUMENTS

| | | | |
|---|---|---|---|
| 2,795,552 | 6/1957 | Abbott et al. | 252/49.7 |
| 4,009,122 | 2/1977 | Lines et al. | 252/431 N |
| 4,164,473 | 8/1979 | Coupland et al. | 252/32.7 |
| 4,192,757 | 3/1980 | Brewster | 252/42.7 |
| 4,248,720 | 2/1981 | Coupland et al. | 252/42.7 |
| 4,474,674 | 10/1984 | Gutierrez et al. | 556/57 |
| 4,889,647 | 12/1989 | Rowan et al. | 252/42.7 |

Primary Examiner—Ellen McAvoy
Attorney, Agent, or Firm—Rasma B. Balodis

[57] ABSTRACT

Novel molybdenum complexes prepared by reacting (a) a fatty oil or acid, (b) 2-(2-aminoethyl)aminoethanol and (c) a molybdenum source are described. The molybdenum complexes impart antifriction, antioxidant, and antiwear properties to lubricating compositions and decrease fuel consumption in internal combustion engines using same.

8 Claims, No Drawings

ORGANIC MOLYBDENUM COMPLEXES

BACKGROUND OF THE INVENTION

The present invention concerns novel organic molybdenum complexes and their use as multifunctional additives for lubricating compositions.

Many attempts to reduce fuel consumption in engines have been mechanical nature. Another approach to the problem is the use of lubricants that reduce the internal friction in the engine, thus resulting in a reduction in the engine's energy requirements. Friction is of particular significance in internal combustion engines, because the loss of substantial amount of theoretical mileage is traceable directly to friction. Friction will increase the power required to effect movement, thus increasing fuel consumption. Therefore, it is advantageous to use lubricants which minimize this friction.

Since various antifriction additives act in a different physical or chemical manner, only some satisfy the effectiveness and compatibility criteria leading to a significant energy loss prevention function of the lubricant. Therefore, it is desirable that the additive possess other functional properties, in particular antiwear and antioxidant functionality.

Molybdenum compounds known to be useful in engine lubricants include certain molybdenum complexes of fatty alkyl amines with a sulfur donor taught in U.S. Pat. No. 4,164,473 and molybdenum complexes of fatty oil and diethanol amine disclosed in U.S. Pat. No. 4,889,647.

It has been now discovered that a novel class of organomolybdenum complexes imparts antifriction, antioxidant and antiwear properties to lubricants resulting in increased energy efficiency.

SUMMARY OF THE INVENTION

In accordance with the present invention, there are provided organic molybdenum complexes prepared by reacting (a) a fatty derivative of 2-(2-aminoethyl)aminoethanol and (b) a molybdenum source sufficient to yield about 0.1 to 20 percent of molybdenum based on the weight of the complex.

Another object of the invention concerns lubricating compositions comprising a major portion of a lubricating oil and a friction reducing amount of said molybdenum complex.

DETAILED DESCRIPTION OF THE INVENTION

The molybdenum complexes of the invention are reaction products of a fatty derivative of 2-(2-aminoethyl)aminoethanol and a molybdenum source. A specific chemical structure cannot be assigned to the product.

It is believed that the major components may have the structural formulae

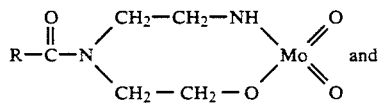 and

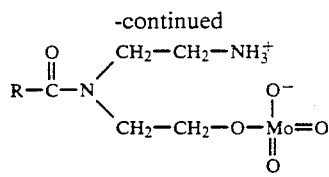

wherein R represents a fatty residue.

The fatty residue may be derived from fatty oils or fatty acids.

The fatty oils are glyceryl esters of higher fatty acids. Such esters are commonly known as vegetable and animal oils. Vegetable oils particularly useful are oils derived from coconut, corn, cottonseed, linseed, peanut, soybean and sunflower seed. Similarly, animal fatty oils such as tallow may be used. The fatty acids may be saturated or unsaturated. Particularly useful are lauric, palmitic, stearic, oleic, linoleic and linolenic acids. Preferred are fatty residues containing at least 12 carbon atoms and may contain 22 carbon atoms and higher.

The source of molybdenum is an oxygen-containing molybdenum compound capable of reacting with the fatty derivative of 2-(2-aminoethyl)aminoethyl to form an ester-type molybdenum complex. The sources of molybdenum include, among others, ammonium molybdates, molybdenum oxides and mixtures thereof.

The fatty derivatives of 2-(2-aminoethyl)aminoethanol may be prepared by hydrolysis of fatty derivatives of 1-(2-hydroxyethyl)-2-imidazoline which are available commercially. The formed amine-amide intermediate is then reacted with a molybdenum source. Alternately, the fatty derivatives may be prepared by reacting about 1.0 to 2.5, preferably 1.0 to 2.0 moles of 2-(2-aminoethyl)aminoethanol per mole of fatty oil. If excess fatty oil is used, part of the monoglyceride formed may react with the molybdenum source to form a molybdenum complex and the remainder will act as a diluent for the product. The entire mixture may be incorporated into the lubricating composition. If fatty acid is used, the preferred mole ratio of fatty acid to the amine is 1:1.

The molybdenum source is added in a sufficient quantity to yield 0.1 to 20, preferably 6.0 to 8.5, optimally about 8 percent of molybdenum per total product.

The molybdenum complexes are prepared by a condensation reaction. The reaction is conducted at elevated temperatures to accelerate said reaction and remove water of reaction. For example, temperatures of about 70° C. to 160° C. may be used depending upon the particular reactants.

The amount of the molybdenum complex in the lubricating composition may range from about 0.01 to 10 percent and preferably, from about 0.1 to 1.0 percent. An amount of 0.01 percent of the molybdenum complex is the minimum effective amount for imparting friction reducing properties to lubricating compositions.

The lubricating compositions contemplated herein include lubricating oils containing a major amount of base oil. The base oil may be selected from oils derived from petroleum hydrocarbon and synthetic sources. The hydrocarbon base oil may be selected from naphthenic, aromatic and paraffinic mineral oils. The synthetic oils may be selected from, among others, alkylene polymers, polysiloxanes, carboxylic acid esters and polyglycol ethers.

The lubricating compositions may contain the necessary ingredients to prepare the composition, as for example, dispersing agents, emulsifiers and viscosity improvers. Depending on the intended use of the lubricant, other functional additives may be added to enhance a particular property of the lubricant. The lubricating compositions may further contain known antioxidants, extreme pressure agents, metal passivators, rust inhibitors and other antiwear and antifriction agents.

The following examples are given for the purpose of further illustrating the invention. All percentages and parts are based on weight unless otherwise indicated.

EXAMPLE 1

A reactor was charged with 1-(2-hydroxyethyl)-2-2-(tall oil alkyl)-2-imidazoline, 150 g, water, 30 g, and molybdenum trioxide, 32 g. The reaction was heated to 130° C. while distilling water. Vacuum was applied and the reaction was heated at 130° to 140° C. for 2 hours. Oil diluent, 50 g, was added and the liquid was filtered. The molybdenum content of the product was 9.72 percent.

EXAMPLE 2

Friction Test

The molybdenum complex of Example 1 was tested for friction reducing properties by a modified Falex ring and block test procedure. This test is believed to simulate the Five Car Fleet Test on laboratory scale.

The Falex machine was stabilized by a break-in run with a base oil (Sunvis® 21 manufactured by Sun Oil Company) for 1 hour at 150° C. under a load of 4.54 kg and for 5 minutes at 114° C., followed by heating at 150° C.

After the break-in period, 100 ml base oil was added and the friction was measured as pound friction force at one minute intervals for 15 minutes at 108° C., 800 rpm and load of 2.27 kg. After draining the base oil and cleaning, the same ring and block was used for testing the sample. The values of pound friction force were converted to coefficient of friction which is defined as a ratio of friction force to applied force and compiled in Table I herein. The results indicate that the molybdenum complex of the invention substantially reduces the coefficient of friction of engine oils.

TABLE I

| | Falex Friction Test | | |
|---|---|---|---|
| | Ingredient, Percent | | |
| Sample | 1 | 2 | 3 |
| Base Oil | 100 | 99.5 | 99.0 |
| Molybdenum Complex | — | 0.5 | 1.0 |
| Cooeficient of Friction | 0.0944 | 0.0918 | 0.0867 |

A laboratory test was conducted by using the original Falex machine to simulate the valve train wear of an automobile engine. The V-blocks and pin were washed in mineral spirits with an ultrasonic cleaner, rinsed with acetone, air-dried and weighed. The test sample (60 g) was placed into the oil cup. The motor was switched on and the loading arm was placed on the ratchet wheel. Upon reaching the reference load of 227 kg, the ratchet wheel was disengaged and the load was maintained constant for 3.5 hours. Thereafter, the motor was switched off. The V-blocks and pin were washed, dried and weighed. The weight loss, a measure of wear, was recorded and compiled in Table II.

The test samples were prepared by adding the compound of Example 1 to the base Motor oil SAE 30, SF (containing 0.11 percent phosphorus and no supplemental antioxidant) in the amount given in Table II. The results indicate that the present compound affords good antiwear properties.

TABLE II

| | Modified Falex Wear Test | | |
|---|---|---|---|
| Sample | Active Ingredient | Percent | Total Weight Loss, mg. |
| 4 | None | — | 73.2 |
| 5 | Compound of Example 1 | 0.5 | 25.6 |
| 6 | Compound of Example 1 | 1.0 | 10.6 |

EXAMPLE 3

Thin Film Oxygen Uptake Test

The test was conducted essentially according to the method described by Chia-Soon Ku et al, *J. Am. Soc. Lubricating Eng.*, 40, 2 75–83, 1984. The oxidation induction time of the lubricant was measured under conditions which simulate the high temperature oxidation processes in automotive engines by a modified rotary bomb oxidation test method ASTM D-2272. The test was conducted with 1.5 gram samples of SAE 30, SF motor oil. The oil was fully formulated (containing 0.11 percent phosphorus and no supplemental antioxidant). The compound of Example 1 was added to the oil in the amount indicated in Table III. The test was conducted at 160° C., and initial oxygen pressure of 620.6 kPa (90 psi). A "pass" oil has a high induction time, while a "fail" oil has a low time. The additive of the invention has good antioxidant properties as indicated by the data compiled in Table III.

TABLE III

| | Thin Film Oxygen Uptake Test | | |
|---|---|---|---|
| Sample | Active Ingredient | Percent | Average Induction Time, Min. |
| 7 | None | — | 107.5 |
| 8 | Compound of Example 1 | 1.0 | 130.0 |

The above embodiments have shown various aspects of the present invention. Other variations will be evident to those skilled in the art and such modifications are intended to be within the scope of the invention as defined by the appended claims.

What is claimed is:

1. An organic molybdenum complex prepared by reacting (a) about 1.0 mole of fatty oil having 12 or more carbon atoms, (b) about 1.0 to 2.5 moles 2-(2-aminoethyl)aminoethanol and (c) a molybdenum source sufficient to yield about 0.1 to 20 percent of molybdenum based on the weight of the complex, the reaction being carried out at about 70° to 160° C.

2. The organic molybdenum complex according to claim 1 wherein the fatty oil is coconut oil and the molybdenum content is 7.0 to 8.5 percent based on the weight of the complex.

3. An organic molybdenum complex prepared by (a) hydrolyzing 1-(2-hydroxyethyl)-2-imidazoline substituted by a fatty residue derived from fatty oil or acid and having 12 or more carbon atoms, to form an amineamide intermediate and (b) reacting with a molybdenum source sufficient to yield about 0.1 to 20.0 percent of molybdenum based on the weight of the complex, the reaction being carried out at about 70° to 160° C.

4. The organic molybdenum complex according to claim 3 wherein the fatty residue is derived from tall oil.

5. A lubricating composition comprising a major amount of a lubricating oil and about 0.01 to 10.0 percent of an organic molybdenum complex prepared by (a) hydrolyzing 1-(2-hydroxyethyl)-2-imidazoline substituted by a fatty residue derived from fatty oil or acid and having 12 or more carbon atoms, to form an amine-amide intermediate and (b) reacting with a molybdenum source sufficient to yield about 0.1 to 20.0 percent molybdenum based on the weight of the complex, the reaction being carried out at about 70° to 160° C.

6. A lubricating composition comprising a major amount of a lubricating oil and about 0.01 to 10.0 present of an organic molybdenum complex prepared by reacting (a) about 1.0 mole of fatty oil having 12 or more carbon atoms, (b) about 1.0 to 2.5 moles 2-(2-aminoethyl)aminoethanol and (c) a molybdenum source sufficient to yield, about 0.1 to 20.0 percent of molybdenum based on the weight of the complex, the reaction being carried out at about 70° to 160° C.

7. A method of reducing fuel consumption in an internal combustion engine which comprises lubricating said engine with a lubricating composition comprising a major amount of a lubricating oil and about 0.01 to 10.0 percent of an organic molybdenum complex prepared by (a) hydrolyzing 1-(2-hydroxyethyl)-2-imidazoline substituted by a fatty residue derived from fatty oil or acid and having 12 or more carbon atoms to form an amine-amide intermediate and (b) reacting with a molybdenum source sufficient to yield about 0.1 to 20.0 percent molybdenum based on the weight of the complex, the reaction being carried out at about 70° to 100° C.

8. A method of reducing fuel consumption in an internal combustion engine which comprises lubricating said engine with a lubricating composition comprising a major amount of a lubricating oil and about 0.01 to 10.0 percent of an organic molybdenum complex prepared by reacting (a) about 1.0 mole of fatty oil having 12 or more carbon atoms, (b) about 1.0 to 2.5 moles 2-(2-aminoethyl)aminoethanol and (c) a molybdenum source sufficient to yield about 0.1 to 20.0 percent of molybdenum based on the weight of the complex, the reaction being carried out at about 70° to 160° C.

* * * * *

UNITED STATES PATENT AND TRADEMARK OFFICE
CERTIFICATE OF CORRECTION

PATENT NO. : 5,137,647
DATED : Aug. 11, 1992
INVENTOR(S) : Thomas J. Karol

It is certified that error appears in the above-identified patent and that said Letters Patent is hereby corrected as shown below:

Column 1, line 10
"have been mechanical nature" should be
-- have been of mechanical nature --;

Column 3, lines 13 to 14
"1-(2-hydroxyethyl)-2-2-(tall oil alkyl)-2-imidazoline" should be
-- 1-(2-hydroxyethyl)-2-(tall oil alkyl)-2-imidazoline --.

Signed and Sealed this

Twenty-fourth Day of August, 1993

*Attest:*

BRUCE LEHMAN

*Attesting Officer*  *Commissioner of Patents and Trademarks*